(12) United States Patent
Israel et al.

(10) Patent No.: US 7,572,774 B2
(45) Date of Patent: Aug. 11, 2009

(54) METHODS FOR TREATING GLUTAMATE CYTOTOXICITY WITH BETA-NAPHTHOQUINONE COMPOUNDS

(75) Inventors: Maurice Israel, Bure-sur-Yvette (FR); Jordi Molgo, Antony (FR); Christian Bloy, Lyons (FR); Cesar Mattei, Herts (GB)

(73) Assignee: Centre National de la Recherche Scientific (C.N.R.S.), Paris (FR)

( * ) Notice: Subject to any disclaimer, the term of this patent is extended or adjusted under 35 U.S.C. 154(b) by 418 days.

(21) Appl. No.: 10/051,243

(22) Filed: Jan. 22, 2002

(65) Prior Publication Data

US 2002/0115617 A1 Aug. 22, 2002

Related U.S. Application Data

(63) Continuation of application No. PCT/FR00/102120, filed on Jul. 21, 2000.

(30) Foreign Application Priority Data

Jul. 21, 1999 (FR) ................................ 99 09469

(51) Int. Cl.
*A01N 43/04* (2006.01)
*A01N 47/10* (2006.01)
*A01N 33/24* (2006.01)
*A61K 31/13* (2006.01)
*A61K 31/70* (2006.01)

(52) U.S. Cl. .............................. 514/35; 514/25; 514/27; 514/481; 514/645; 514/646

(58) Field of Classification Search .................. 514/25, 514/27, 35, 36, 481, 590, 645, 646
See application file for complete search history.

(56) References Cited

U.S. PATENT DOCUMENTS

| 5,158,976 | A | * | 10/1992 | Rosenberg |  |
|---|---|---|---|---|---|
| 5,254,683 | A |  | 10/1993 | Chapdelaine et al. |  |
| 5,523,322 | A | * | 6/1996 | Blache et al. | 514/481 |
| 6,384,069 | B1 | * | 5/2002 | Feuerstein et al. | 514/409 |

FOREIGN PATENT DOCUMENTS

| EP | 0 146 338 | 6/1985 |
|---|---|---|
| EP | 0 631 777 | 1/1995 |

| WO | WO98/51291 | 11/1998 |
|---|---|---|

OTHER PUBLICATIONS

Mattei et al., "Naftazone reduces glutamate cerebro spinal fluid levels in rats and glutamate release from mouse cerebellum synoptosomes", Neuroscience Letters, vol. 271, pp. 183-86, 1999.*
Neiva et al., "Aluminum induces lipid peroxidation and aggregation of human blood platelets", Brazilian Journal of Medical and Biological research, vol. 30, pp. 599-604, 1997.*
Neu et al., "Platelet aggregation and multiple sclerosis", Acta neurol. scandinav., vol. 66, pp. 497-504, 1982.*
Lechner et al., "Parkinsons with a high vascular risk - Lechner-Ott Syndrome", Wiener medizinische Wochenschrift, vol. 136, No. 15-16, pp. 387, 388, 390, and 391, 1986.*
Accession No. 97018149: Rao et al., Indian Journal of physiology and pharmacology, (Jan. 1996) vol. 40, No. 1, pp. 5-14.*
Accession No. 1998334761: Li et al., American Journal of Alzheimer's Disease, (1998) vol. 13, No. 5, pp. 236-244.*
Rao et al., Indian Journal of Physiology and Pharmacology, Jan. 1996, vol. 40, No. 1, pp. 5-14.*
Sharma et al., "Platelet Aggregation in Patients with Parkinson's Disease", Stroke, a Journal of Cerebral Circulation, Dec. 1991, vol. 22, No. 12, 1607-08.*
Mattei et al., "Naftazone reduces glutamate cerebro spinal fluid levels in rats and glutamate release from mouse cerebellum synaptosomes," *Neuroscience Letters*, 1999, pp. 183-186, vol. 271, Elsevier Science Ireland Ltd., Ireland.
Azza et al., "Lipid Peroxidation and Lysosomal Integrity in Different Inflammatory Models in Rats: The Effects of Indomethacin and Naftazone," *Pharmacological Research*, 1995, pp. 279-285, The Italian Pharmacological Society, Italy.
Zicot, "Etude multicentrique de l'efficacite et de la tolerance de la naftazone (Mediaven® 10 MG). Comaparaison de deux schemas posologiques," *Revue Medicale De Liege*, Apr., 1993. pp. 224-228, France.
Herber et al., "Reduction and Glucuronidation of Naftazone by Human and Rat Liver Microsomes," *Drug Metabolism and Disposition*, 1995, pp. 1305-1314, vol. 23, No. 12, The American Society for Pharmacology and Eperimental Therapeutics, Bethesda, Maryland, USA.

* cited by examiner

*Primary Examiner*—Traviss C McIntosh, III
(74) *Attorney, Agent, or Firm*—Buchanan, Ingersoll & Rooney P.C.

(57) ABSTRACT

The present invention relates to the use of beta-naphthoquinone derivatives, and salts thereof, for the prevention and/or the treatment of glutamate cytotoxicity. It further relates to the use of beta-naphthoquinone derivatives, and salts thereof, for preventing and/or treating glutamate induced neurological disorders. Additionally, it concerns the use of beta-naphthoquinone derivatives, and salts thereof, for making drugs exerting an inhibitory effect on the release of glutamate.

2 Claims, 2 Drawing Sheets

METHODS FOR TREATING GLUTAMATE CYTOTOXICITY WITH BETA-NAPHTHOQUINONE COMPOUNDS

Figure 1:
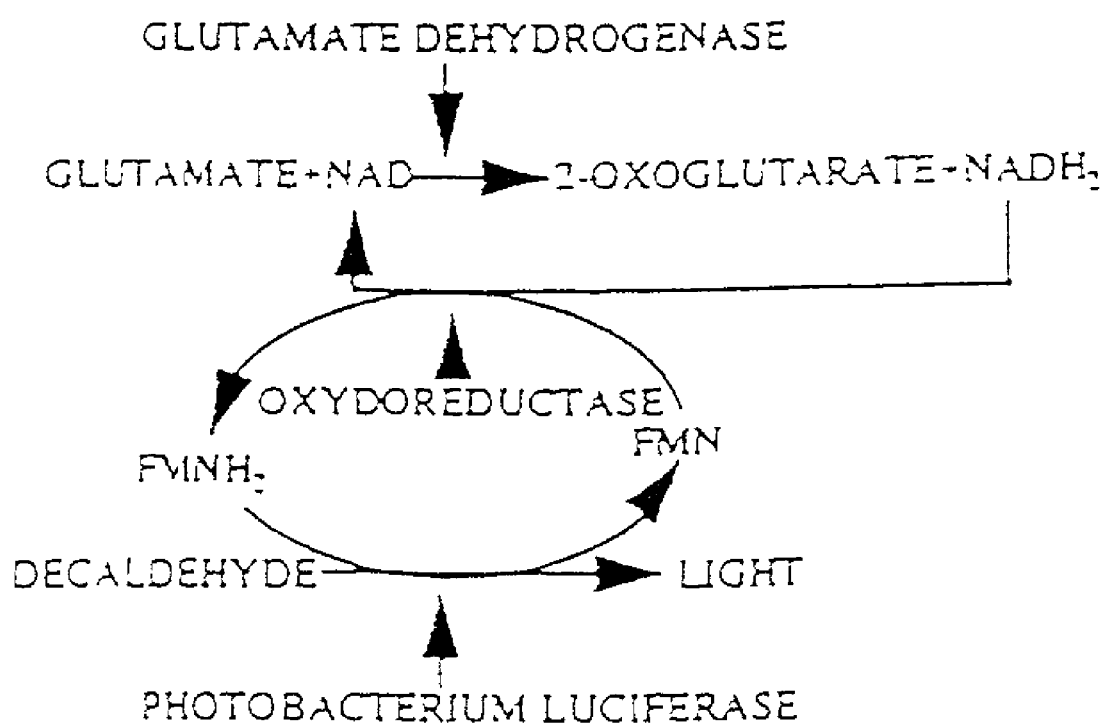

This application is a continuation-in-part International Application No. PCT/FR00/02120 filed on Jul. 21, 2000, which International Application was not published by the International Bureau in English on Jan. 25, 2001. This application also claims priority under 35 U.S.C. §§ 119 and/or 365 to FR 99/09469 filed in France on Jul. 21,1999. The entire content of both of the above-mentioned PCT and French applications are hereby incorporated by reference.

The present invention relates to the use of beta-naphthoquinone derivatives, and salts thereof, for the prevention and/or the treatment of glutamate cytotoxicity. It further relates to the use of beta-naphthoquinone derivatives, and salts thereof, for preventing and/or treating glutamate induced neurological disorders. Additionally, it concerns the use of beta-naphthoquinone derivatives, and salts thereof, for making drugs exerting an inhibitory effect on the release of glutamate.

A large number of studies have established that cellular communication using excitatory amino acids can be transformed into a mechanism of cell destruction.

Glutamate is the main excitatory neurotransmitter in the nervous system, especially brain and spinal cord, of mammals wherein it is working at a variety of excitatory synapses.

The ubiquitous distribution of glutamate receptors throughout the nervous system proves that glutamate plays a central role in a wide range of physiological as well as pathological events (Watkins J. C , Collingridge G. L., The NMDA receptor, IRL Oxford, 1989). It is for example strongly suggested that it plays a central role in functions such as learning, pattern recognition, and memory (Bliss T. V. P. Collingridge G. L., Nature 361, 31–39, 1993).

Normally extracellular levels of glutamate are elevated only in a brief and spatially localized fashion associated with normal synaptic transmission however, under pathologic circumstances levels may remain dramatically increased.

Additionally, it has also been known for decades that glutamate is toxic to neurons in vitro and in vivo and that the function of glutamate receptor, especially glutamate receptors of the N-methyl-D-aspartate ("NMDA") receptor subtype, is crucial in a number of neuronal damages and injuries (Appel S. H., Trends Neurosci. 16, 3–5, 1993). Many neurological disorders involving epileptic seizures and chronic or acute degenerative processes, such as for example Alzheimer's, Huntington's, Parkinson's diseases, multiple sclerosis (MS), amyotrophic lateral sclerosis (ALS), spinal muscular atrophy (SMA), retinopathy, stroke and traumatic brain injury, involve neuronal cell death caused by over-stimulation of the glutamate receptors. Similarly, it has been shown that neuronal injury caused by ischemla after occlusion of cerebral arteries could, at least partially, be mediated by excessive activation of glutamate receptors as in the ischemic brain, extracellular glutamate is elevated rapidly after the onset of isohemia and declines following reperfusion (Davalos et al., 1997, Stroke, 28, 708–710). Other pathologic circumstances associated with dramatic increase of extracellular glutamate levels are hypoxia or hypoglycaemia. Finally, Stephans and Yamamoto (1994, Synapse ,17, 203–209) have shown that drug-induced neurotoxicity, for example neurotoxic effects of methamphetamine (METH) on striatal dopaminergic neurons, could actually be mediated by over-stimulation of the glutamate receptors.

These excessive activations of glutamate receptors, referred to as "glutamate cytotoxicity", are actually associated with the elevation of extracellular glutamate levels. The mechanisms of the elevation of extracellular glutamate include enhanced efflux of glutamate and/or the reduction of glutamate uptake by cells. Thus, it would be desirable to provide a means of protecting affected cells, especially neurons, from glutamate-induced cytotoxicity, and more specifically to provide means of regulating glutamate release and/or uptake by glutamate producing cells.

To this end, it has already been proposed to target the glutamate receptors, mostly the N-methyl-D-aspartate ("NMDA") receptor, present on the targeted cells by inhibiting them by the use of agonist or antagonist specific molecules. Examples of such molecules are anthranilic acid derivatives (see U.S. Pat. No. 5,789,444), Basilen Blue D-3G (Reactive Blue 2) and Cibacron Blue 3GA and 5-adenylylimidodiphosphate (AMPPNP) (see U.S. Pat. No. 6,326,370), NMDA specific antagonists such as ketamine, dextromophan, or 3-(2-carboxypiperazin-4-yl)-propyl-1-phosphonic acid (Kristensen et al., 1992, Pain, 51:249–253; Eide et al., 1995, Pain, 61,221–228), or the 2-methyl-6-(phenylethynyl)pyridine (MPEP) which is an antagonist of the metabotropic glutamate receptor subtype 5 (mGluR5) (Ossowska et al., 2001, Neuropharmacology,41, 413–420).

However, widespread use of these compounds is precluded by their undesirable side effects (e.g. psychotomimetic effects, headache, hallucinations, dysphoria or disturbances of cognitive and motor functions). Thus, the available treatment methods are not satisfactory in terms of safety or efficiency for their wide implementation.

Therefore, there is still a need in the provision of improved methods and means for protecting affected cells, and more preferably neurons, from glutamate-induced cytotoxicity.

The investigation by the inventors has now surprisingly shown that certain beta-naphthoquinone derivative compounds, previously used as vasoprotective drugs, have preventing and/or treating effects on glutamate-induced cytotoxicity. More specifically, said compounds have been shown to control, and preferably inhibit, the spontaneous and/or the evoked (i.e. the glutamate release by cells in response to depolarization) release of glutamate.

Thus the present invention provides a new class of compounds which represents a pharmacological alternative to previously described compounds, such as competitive and nor-competitive glutamate antagonists or agonists, gangliosides and growth factors, for the treatment or prevention of acute and chronic glutamate-related diseases or conditions, particularly neurological diseases. In preferred embodiments, the present invention provides a new class of compounds which can be used as pharmacological tools for the modulation of glutamate cellular release and cytotoxicity, preferably neurotoxicity, and which allows the possible treatment and/or prevention of many neurological disorders involving epileptic seizures and acute and chronic neurodegenerative diseases, as well as neuronal injury caused by ischemia or glutamate-related diseases or conditions, wherein said disorders are, at least partially, associated with excessive activation of glutamate receptors and/or with excessive extracellular glutamate levels.

The invention is therefore first directed to a novel use of beta-naphthoquinone derivatives for making drugs with an inhibitory effect on the extracellular glutamate release, wherein said derivatives are selected among the group consisting of:

(i) compounds having the formula (I):

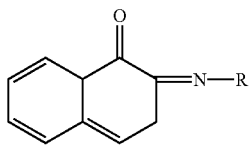

wherein R represents —NH—CO—NH$_2$, —NH—CO—CH$_3$, or —OH group, (ii) glucuronide derivatives thereof having the formula (II):

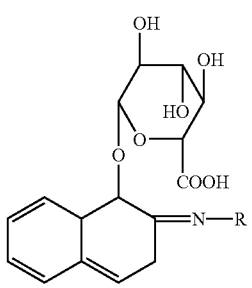

(iii) addition salts thereof.

According to preferred embodiments, said derivatives are selected among the group consisting of the 1,2-naphthoquinone, 2-semicarbazone, also called naftazone according to its international common name, and its corresponding glucuronidated derivative, i.e. the 1-(1-hydroxy,2-naphthyl)semicarbazide-1-β-O-gluco-pyranosiduronco acid, respectively of formula (III) and formula (IV):

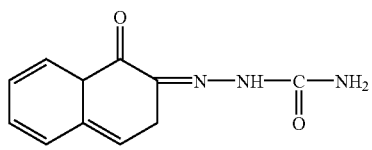

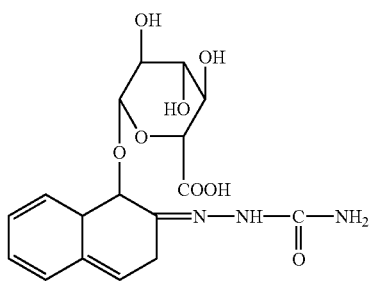

In special embodiment, the derivatives of the invention are further substituted with, one to four, identical or different, heteroatoms and/or hetero groups. Examples of said heteroatoms and/or hetero groups are O, H, alkyl groups $C_nH_{n-1}$, with (n=1 to 5, OCH$_3$, N, halogens (for example F or Br) S or any labeling element allowing to visualize said derivatives. These substituting atoms or groups, and their uses, are widely known in the art.

The addition salts of the derivatives of the invention comprise conventional salt formed from inorganic or organic acids or bases, such as hydrochloric, hydrobromic, sulfuric, phosphoric, nitric, perchloric, fumaric, acetic, sodium, lithium, potassium, magnesium, aluminium, calcium, zinc, ethylenediamine; formic, benzoic, maleic, tartaric, citric, oxalic, aspartic acid, and alkane-sulfonic acids is even mentioned.

The preparation of compounds used according to the invention has been widely described in the literature, for example, in BSM 924 M or Patent FR 2103 504.

The newly identified inhibitory properties of these compounds, reported in the examples hereafter, make them particularly suitable for treating and/or preventing diseases, conditions and attacks related to deleterious effects of glutamate released in exess, and preferably neurological ones.

Thus the present invention further relates to a method for treating and/or preventing glutamate-evoked cytotoxicity in a patient in need thereof comprising administering to said patient a composition containing a therapeutically effective amount of at least one beta-naphthoquinone derivative and a pharmaceutically acceptable carrier, wherein said derivative is selected among the group consisting of:

(i) compounds having the formula (I):

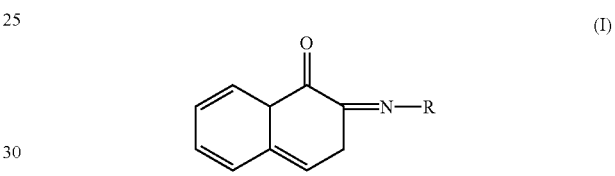

wherein R represents —NH—CO—NH2, —NH—CO—CH3, or —OH group, and (ii) glucuronide derivatives thereof having the formula (II):

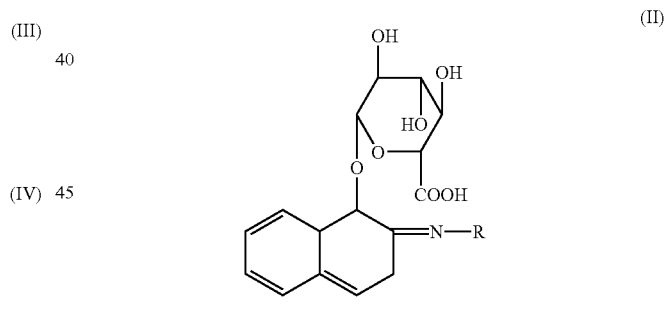

wherein R is as above indicated, and (iii) addition salts thereof.

In preferred embodiments, the derivatives administered according to the method of the invention are selected among the group consisting of the 1,2-naphthoquinone, 2-semicarbazone, also called naftazone, and its corresponding glucuronidated derivative, i.e. the 1-(1-hydroxy,2-naphthyl)semicarbazide-1-β-O-glucopyranosiduronic acid (see Formula (III) and (IV) respectively). Similarly, these derivatives might be substituted with, one to four, identical or different, heteroatoms and/or hetero groups as defined above.

The term "glutamate-evoked cytotoxicity" within the present invention is intended to designate cell toxicity associated with excessive activations of glutamate receptors. These terms are well known by the one skilled in the art. More specifically, the "glutamate-evoked cytotoxicity" concerns all affected cells expressing glutamate receptors. According to preferred embodiments, these affected cells are nervous cells (i.e. neuro-cells), preferably neurons. These affected nervous cells are, for example, present in brain, spinal cord, retina, at the neuro-muscular junction, etc . . . "Cytotoxicity" means that the cell functions and/or properties are affected, leading to cell malfunctioning, and finally to cell death.

In a particularly preferred embodiment, the method of the invention is intended for treating and/or preventing glutamate-evoked neurotoxicity, and even more preferably for treating and/or preventing neurodegeneration (i.e. degeneration of nervous cells).

The present invention further relates to a method for modulating the release of glutamate in a patient comprising administering to said patient a composition containing a therapeutically effective amount of at least one beta-naphthoquinone derivative and a pharmaceutically acceptable carrier, wherein said derivative is selected among the group consisting of derivatives of Formula I to IV, and addition salts thereof. These derivatives are detailed above.

"Modulating the release of glutamate" means that the levels of released glutamate in non treated patient is different from the one observed after his treatment with the derivatives of the invention. According to preferred embodiment, treatment of the patient with the derivatives of the invention leads to a negative modulation, preferably to the inhibition, of the glutamate release by the producing cells, and thus to a decreased glutamate level in the treated patient compared to the glutamate level observed before said treatment.

The present invention further relates to a method for treating and/or preventing disease and/or condition associated with the excessive release of glutamate in a patient comprising administration to said patient of a composition containing a therapeutically effective amount of at least one beta-naphtoquinone derivative and a pharmaceutically acceptable carrier, wherein said derivative is selected among the group consisting of derivatives of Formula I to IV, and addition salts thereof. These derivatives are detailed above.

"Disease and/or condition associated with the excessive release of glutamate" is intended to designate large number of acute and chronic glutamate-related diseases or conditions, particularly neurological diseases. It designates more specifically epileptic seizures and acute and chronic neurodegenerative diseases, as well as neuronal injury caused by ischemia or glutamate-related diseases or conditions, wherein said disorders are, at least partially, associated with excessive activation of glutamate receptors and/or with excessive extracellular glutamate levels. Examples are involving chronic or acute degenerative disorders, such as for example Alzheimer's, Huntington's, Parkinson's diseases, multiple sclerosis (MS), amyotrophic lateral sclerosis (ALS), spinal muscular atrophy (SMA), retinopathy, stroke and traumatic brain injury, involve neuronal cell death caused by over-stimulation of the glutamate receptors. Similarly, neuronal injury caused by ischemia or drug-induced neurotoxicity, for example neurotoxic effects of methamphetamine (METH) on striatal dopaminergic neurons, are indications of the methods according to the present invention. Other indications are glutamate-related conditions such as for example pain, hormonal balance, blood pressure, thermoregulation, respiration, learning, pattern recognition or memory, or any disorder subsequent to hypoxia or hypoglycaemia.

For example, the treatment of epilepsy, amyotrophic lateral sclerosis, spinal muscular atrophy (SMA), Huntington's disease, deleterious effect due to excesses of glutamate released as a result of cerebral accidents of traumatic or otner vascular origin will be mentioned.

The derivatives described herein are administered as a composition containing at least one active compound and a pharmaceutically acceptable carrier. In preparing such a composition, any conventional pharmaceutically acceptable carrier can be utilized. The carrier material can be an organic or inorganic inert carrier material suitable for the selected route of administration. Suitable carriers include water, gelatin, gum arabic, lactose, starch, magnesium stearate, talc, vegetable oils, polyalkylene-glycols, petroleum jelly and the like. Furthermore, the pharmaceutical composition may contain other pharmaceutically active agents. Additional additives such as flavoring agents, preservatives, stabilizers, emulsifying agents, salts for varying the osmotic pressure, buffers and the like may be added in accordance with accepted practices of pharmaceutical compounding. Any conventional form such as tablets, capsules, pills, powders, granules, and the like may be used. Advantageously, they are in the form of tablets, sugar coated tablets, hard gelatin capsules, capsules, granules, for oral administration, or solutions or suspensions for administration via an injectable channel.

The methods of the invention may be carried out by administering the composition containing derivative of the invention by any route whereby drugs are conventionally administered. Such routes include systemic and local routes. Examples are intravenous, intramuscular, subcutaneous, intracranial, intraperitoneal, as well as oral routes. Preferably, the method of the invention is carried out via oral or intravenous routes of administration.

In accordance with this invention, the derivatives described herein are useful in pharmaceutically acceptable oral modes. A preferred oral dosage form comprises tablets, capsules of hard or soft gelatin, methylcellulose or of another suitable material easily dissolved in the digestive tract. The oral dosages contemplated in accordance with the present invention will vary in accordance with the needs of the individual patient as determined by the prescribing physician. The preferred oral dosage form is capsules or tablets containing from 50 to 500 mg of a derivative of the invention.

Typical preparations for intravenous administration would be sterile aqueous solutions including water/buffered solutions. Intraveneous vehicles include fluid, nutrient and electrolyte replenishers. Preservatives and other additives may also be present such as antibiotics and antioxidants. Compositions for bolus i.v. administration may contain up to 10 mg/ml (10,000 mg/liter) of derivative described herein. Compositions for i.v. administration preferably contain from about 50 mg/liter to about 500 mg/liter of at least one derivative described herein.

In carrying out the method of the invention, derivative of the invention is generally given to adults daily, preferably orally or intravenously, in an amount of from about 5 mg/kg to about 30 mg/kg daily, in single or divided doses, preferably from about 13 mg/kg to about 17 mg/kg daily, with the precise dosage being varied depending upon the needs of the patient. The doses will be adapted according to the patient and the pathology to be treated and are for example 1 mg-100 mg/day. In general, this therapy is carried out for a period of about three months. Alternatively, the method of the invention may be carried out prophylactically for an indefinite time in those patients who are have a high risk of suffering an acute neurotoxic event, such as a stroke. For the treatment of an acute neurotoxic event, the patient should be treated in accordance with the method of the invention as soon as possible after the diagnosis of the acute neurotoxic event, preferably within twelve hours, and most preferably within six hours, of the onset of the neurotoxic event. When the drug is administered orally, it is generally administered at regular intervals.

These drugs are notably administered orally or via an injectable channel.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the claims, the invention may be practiced otherwise than as specifically described.

All of the above cited disclosures of patents, publications and database entries are specifically incorporated herein by reference in their entirety to the same extent as if each such individual patent, publication or entry were specifically and individually indicated to be incorporated by reference.

Examples below, demonstrate that the beta-naphthoquinone derivatives described herein inhibit both the spontaneous and evoked-release of glutamate.

Figure 2A:
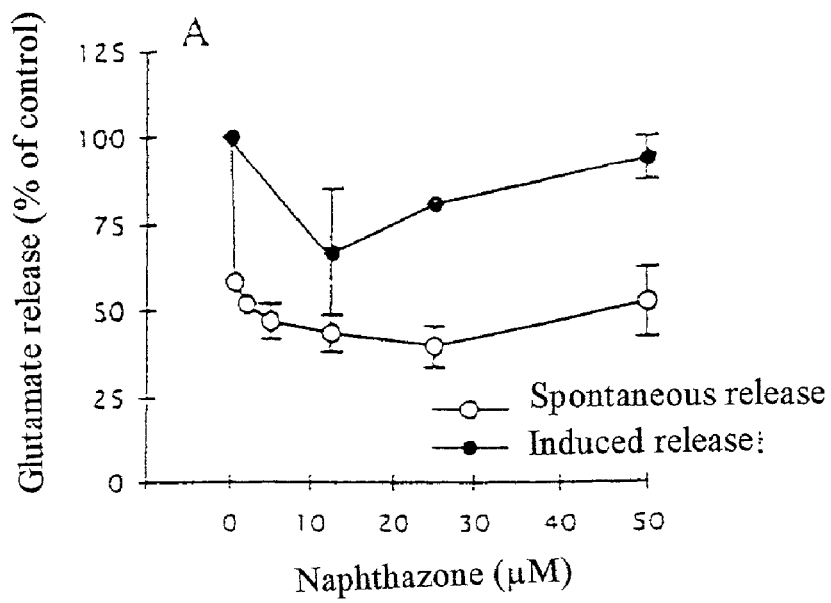
Figure 2B:
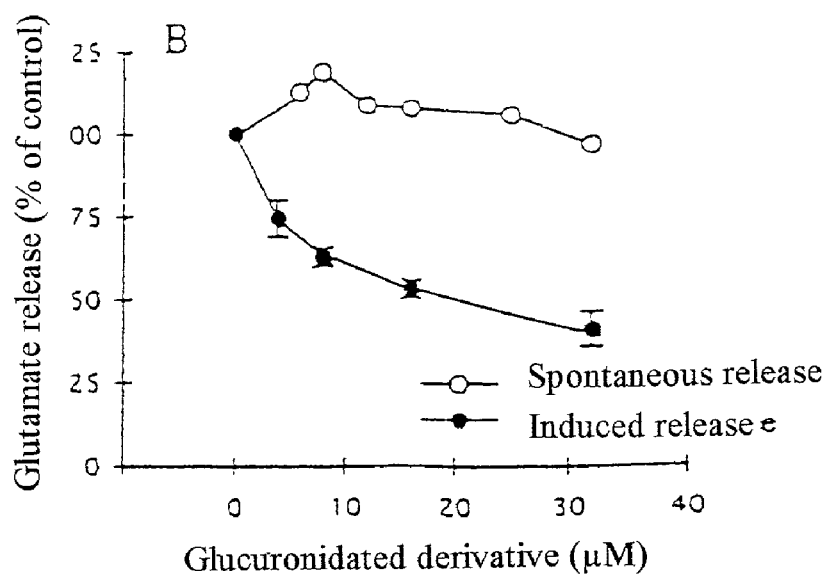

Other features and advantages of the invention are given in the following examples, wherein reference is made to FIGS. 1 and 2, wherein respectively:

FIG. 1 represents the diagram illustrating the chemiluminescence measurement protocol, and FIG. 2 represents the spontaneous release of glutamate and the induced one versus the concentration of naftazone (FIG. 2A) or of its glucuronidated derivative (FIG. 2B).

EXAMPLE 1

Study of the Inhibitory Effects on Glutamate by Naftazone and its Glucuronidated Derivative A: Study of the Effect of a Continuous Treatment with Naftazone for 15 Days on the Glutamate Levels in the CSF (Cerebrospinal Fluid) of Normal Rats Sprague-Dawley rats weighing 200–220 g and Swiss-Webster mice of both sexes, aged 4–8 weeks, are used.

The animals are kept in cages, in a well-ventilated room at 23–24° C., with a light/darkness cycle of 12 hours.

In order to investigate the CSF glutamate levels in the controls, or after treatment with naftazone, the male rats are divided into 3 groups:

Group I (n=8) is used as control. The rats of this group are fed per os for 15 days with the same carrier as the one used for solubilizing naftazone, i.e. 1% methylcellulose Sigma.

The animals of groups II (n=5) and III (n=5) are fed per os for 15 days with 10 and 100 mg of naftazone per kg, per day, respectively, given as a single bolus.

The CSF of anaesthetized rats with 6% pentobarbital (i.p.) is collected by operating according to the usual procedures.

The animals are then decapitated. The CSF samples are centrifuged at 6,000 g for 10 min at 10° C.

The supernatant is extracted, the sediment containing the blood deposits is removed.

The samples are held in 2.5% trichloracetic acid and kept at −80° C.

Ether is used for washing trichloracetic acid off the samples.

In order to determine the glutamate levels in the CSF, chemiluminescence measurements are conducted according to the procedure described in the diagram given in FIG. 1 The reaction is based on the oxidization of glutamate into 2-oxoglutarate under the action of glutamate dehydrogenase, which produces NaDH2, evaluated by using the chemiluminescent reaction of photobacterium.

The CSF samples are tested by adding a known volume of sample to the reaction medium which contains 250 µl of saccharose (120 mM) in Tris buffer (120 mM, pH 7.2), 50 µl of an enzymatic mixture of AND, DMN, NADH-FMN oxidoreductase, luciferase and GDH, and 5 µl of n-decyl aldehyde.

The light emitted by the Luminescent reaction consecutive to the oxidization of L-glutamate and to the production of NADH, is detected by a photomultiplier unit, recorded and calibrated by comparing it with light emitted by a glutamate standard.

Statistical analysis of the data is carried out by using Student's t test for unpaired samples. The values are expressed as average +/− SEM, n=number of animals or experiments carried out.

The data are considered as significantly different from the controls, at $p<0.05$.

The control rats (Group I) which have received the methylcellllose carrier for 15 days, have a CSF glutamate content from 16–34 nmol ml$^{-1}$ with an average value of 22.1+/−6.3 nmol ml$^{-1}$ (n=8).

The daily treatment of rats (groups II and III) for 15 days with a naftazone dose of 10 or 100 mg/kg show that the CSF glutamate content in both groups of rats is 8.1 +/−1.8 (n=5) and 10.8 +/−3.3 ml$^{-1}$ (n=5) respectively.

These results show that the glutamate content in the CSF of rats treated with both naftazone doses is significantly reduced ($p=0.001$ and $p=0.004$, respectively), as compared with the controls.

Furthermore, no significant difference in CSF glutamate content is observed between both groups of rats treated with naftazone, which shows that the effect of the drug is not dose-dependent.

B: Study of the effect of naftazone and of its glucuronide derivatives on the release of glutamate from synaptosomes of mouse brains.

In order to prepare the synaptosomes of mossy fibers, the Swiss-Webster rats are decapitated and the cerebellum is rapidly removed. Small pieces of tissue (1–2 mm³) are washed in 100 ml of a mammal saline standard solution containing (mM): NaCl, 136; KCl, 5.6; MgCl$_2$ 1.2; CaCl$_2$ 2.2; glucose 5.5; NaHCO$_3$ 7.5; NaHPO$_4$/Na$_2$HPO$_4$ buffer 1.2.

An oxygen current is caused to flow through them for 10 minutes.

In order to dissociate the pieces, they are sucked in a reciprocal movement with a 1 ml pipette.

The homogenate obtained is diluted in 3 ml of mammal Krebs's solution and is filtered through a Nylon® tissue (mesh 50 µm).

The filtrate is collected and left to settle for 30–45 min by gravity.

Synaptosomes derived from the glutarmatergic mossy fibers settle because or their large size with the nuclear fraction. The supernatant is discarded and the sediment is resuspended in 1 ml of a standard solution. The release of glutamate from the synaptosomes is detected according to the technique used for evaluating it in the CSF.

FIGS. 2A and 2B show the effects of naftazone (at concentrations of 0.5–50 µM) and of its glucuronidated derivative, respectively, on the spontaneous release of glutamate (curve -o-) and of that induced by depolarization (curve -•-).

Each point in A and B represents the ISEM average of 3 measurements carried out in triple. In A, the spontaneously released glutamate is continuously measured during an exposure of 1 hour to the tested drug and is compared with controls. Release of glutamate by depolarization is determined after a 1 hour exposure to the tested drug and is compared with controls.

The drugs are left to incubate for 1 hour with synaptosomal aliquots before the measurement.

The release of glutamate in response to the depolarization induced by a medium with a high $K^+$ content (30 mM) containing $Ca^{2+}$ (5 mM) is not significantly affected by naftazone at the investigated concentration values.

However, as FIG. 2A shows, naftazone reduces the spontaneous release of glutamate from synaptosomes. The inhibitory effect of naftazone on the spontaneous release of glutamate is already observed at the lowest concentration of drug used (0.5 µM). This effect is maximal at the concentration of 25 µM.

Higher concentrations do not seem to further increase the inhibitory effect.

When the effect of the glucuronidated derivative on the spontaneous release and on that caused by $K^+$ is evaluated, it is seen that the drug does not reduce the spontaneous release of glutamate in the range of the concentrations used.

However, as FIG. 2B shows, the glucuronidated derivative reduces, in a dose-dependent way, the release induced by a medium with a high $K^+$ content (20 mM) containing $Ca^{2-}$ (5 mM).

The maximum reduction (about 60%) is observed at the highest concentration of the tested drug (32 µM).

EXAMPLE 2

Manufacture of Pharmaceutical Compositions

By operating according to the conventional techniques, tablets are made containing:
naftazone: 10 mg
excipient qsp for 100 mg or injectable solutes containing:
naftazone: 5 mg
sterile water asp: 2 ml.

What is claimed is:

1. A method for treating Parkinson's disease in a patient comprising administration to said patient of a composition containing a therapeutically effective amount of at least one beta-naphthoquinone derivative and a pharmaceutically acceptable carrier, wherein said beta-naphthoquinone derivative is selected among the group consisting of:

(i) compounds having the formula (I):

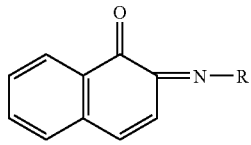

(I)

wherein R represents —NH—CO—NH2, —NH—CO—CH3, or —OH group, (ii) glucuronide derivatives thereof having the formula (II):

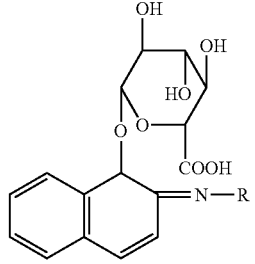

(II)

wherein R is as indicated in (i), and (iii) addition salts thereof.

2. The method of claim 1, wherein said beta-naphthoguinone derivative is selected from among the group consisting of the 1,2-naphthoquinone, 2-semicarbazone and the 1-(1-hydroxy,2-naphthyl)semicarbazide-1-β-O-gluco-pyranosiduronic acid.

* * * * *